United States Patent [19]

Miner

[11] Patent Number: 5,863,547
[45] Date of Patent: Jan. 26, 1999

[54] GLUTARALDEHYDE PLUS ALCOHOL PRODUCT

[75] Inventor: Norman Miner, Arlington, Tex.

[73] Assignee: Healthpoint, Ltd., San Antonio, Tex.

[21] Appl. No.: 806,105

[22] Filed: Feb. 25, 1997

[51] Int. Cl.⁶ .................................................. A01N 25/02
[52] U.S. Cl. ........................... 424/405; 424/406; 514/705
[58] Field of Search ..................................... 424/405, 406; 514/693, 698, 705

[56] References Cited

U.S. PATENT DOCUMENTS

| | | |
|---|---|---|
| 3,016,328 | 1/1962 | Pepper et al. . |
| 3,282,775 | 11/1966 | Stonehill . |
| 3,697,222 | 10/1972 | Sierra . |
| 3,912,809 | 10/1975 | Rendon ..................................... 424/75 |
| 3,917,850 | 11/1975 | Boucher . |
| 4,103,001 | 7/1978 | Schattner . |
| 4,469,614 | 9/1984 | Martin . |
| 4,851,449 | 7/1989 | Bruckner . |
| 5,348,678 | 9/1994 | Hodam et al. .......................... 252/103 |

FOREIGN PATENT DOCUMENTS

| | | |
|---|---|---|
| 251743 | 1/1988 | European Pat. Off. . |
| 279704 | 8/1988 | European Pat. Off. . |

OTHER PUBLICATIONS

Rollin E. Pepper and Velma L. Chandler, Mar. 13, 1963, pp. 384–388, Sporicidal Activity of Alkaline Alcoholic Saturated Dialdehyde Solutions, Department of Microbiology, Ethicom, Inc., Somerville, New Jersey.

Robison et al., vol. 62 1996, pp. 2682–2685, Culture Variability in Tuberculocidal Testing, Appl. Environ. Microbiol.

Scott: Sterilazation—3rd Edition of Block, 1980 or Later.

Strong: Abstract of EP 279704, Aug. 1988.

Whiteley: Abstract of EP 251743, Jan. 1988.

*Primary Examiner*—Neil S. Levy
*Attorney, Agent, or Firm*—Zarley, McKee, Thomte, Voorhees & Sease

[57] ABSTRACT

An aqueous formula is disclosed that combines a relatively low concentration of glutaraldehyde with very low concentrations of alcohol in a stabilizing alkaline buffer system. This formula is sporicidal within 10 hrs. at 20° C., and bactericidal, fungicidal, tuberculocidal, and virucidal within 20 min. at 20° C.

9 Claims, No Drawings

GLUTARALDEHYDE PLUS ALCOHOL PRODUCT

FIELD OF THE INVENTION

The present invention relates to an improved glutaraldehyde-based composition for the high-level disinfection and/or sterilization of heat-sensitive medical, dental, and veterinary reusable devices.

BACKGROUND OF THE INVENTION

Medical, dental and other instruments are often made of high quality stainless steel that can be cleaned and sterilized between uses for different patients by high temperature steam under pressure. This sterilization procedure is quick, reliable, odorless, non-toxic and inexpensive. In contrast to this situation, more and more instruments are now made of heat-sensitive plastic, rubber, glass lenses and electronic components. These flexible, flexible-lensed, and rigid-lensed instruments allow relatively non-invasive diagnostic and treatment procedures within the body.

The non-invasive procedures allowed by these heat-sensitive instruments are responsible for great advances in medical practice. During use, these instruments can be contaminated with deadly pathogens such as the Human Immunodeficiency Virus (HIV), hepatitis viruses, and antibiotic drug-resistant tuberculosis and other bacteria. For these reasons, it is imperative that these heat-sensitive instruments be sterilized of all microbes prior to each use.

One of the problems associated with sterilizing medical instruments is that since many contain plastic and rubber materials, and/or contain lenses positioned with glue, or electrical or other materials, they cannot withstand sterilization by the heat of a steam sterilizer or dry heat oven. One method for sterilizing these devices includes low temperature ethylene oxide gas sterilization systems. However, these systems are very slow and require 24 or more hours of turn-around time.

Aqueous solutions of about 2.5% alkaline glutaraldehyde have been used to disinfect heat-sensitive medical devices since the 1960's. However, these glutaraldehyde solutions have many problems. First, while glutaraldehyde is far more antimicrobial especially against bacterial spores, at alkaline pH values than at acid pH values, in some compositions the glutaraldehyde becomes unstable when the pH value is increased from about 4.0 to about 8.5. Forty percent (40%) of the original glutaraldehyde concentration can be lost within two weeks at pH 8.5. To compensate for this loss of glutaraldehyde, the concentration of glutaraldehyde is originally set at twice the concentration needed for antimicrobial activity. Further, glutaraldehyde is a sensitizing, irritating, and toxic chemical. Thus, when the concentration of glutaraldehyde is doubled to compensate for instability, the toxicity is also increased.

Furthermore, the sporicidal activity of glutaraldehyde is relatively slow requiring an exposure time of ten (10) hours at 25° C. Current compositions of glutaraldehyde may contain salts of acetic acid and glutaraldehyde concentrations of 3.5% to maximize sporicidal activity. This high concentration of glutaraldehyde in combination with the acrid fumes of acetic acid cause still further problems of chemical irritation and toxicity.

Slow tuberculocidal activity is another disadvantage of current glutaraldehyde compositions. They require 45 minutes of exposure at 25° C. for 100% kill of populations of mycobacteria (TB). The increased temperature of 25° C. as compared to 20° C. has been used as an effort to increase the sporicidal and tuberculocidal properties of current glutaraldehyde compositions. Consequences of the increased temperature of 25° C. is that users must provide heating devices, and the toxic glutaraldehyde fumes are further increased.

It can therefore be seen that there is a continuing need for an effective, practical, safe, affordable sterilant for heat-sensitive instruments, as well as for all applications that are beyond the scope of steam sterilization. This invention has as its primary objective the fulfillment of this need.

The inventor has now discovered that small concentrations (5% to 20%) of alcohol improve the tuberculocidal activity of glutaraldehyde. By improving the tuberculocidal activity of a glutaraldehyde composition, it is then possible to lower the concentration of glutaraldehyde and the recommended use temperature. The lower glutaraldehyde concentration and the lower use temperature decrease the toxicity of glutaraldehyde and eliminate the inconvenience of a heating device.

A buffer system can be selected that increases the pH value of the composition to about 7.2 without causing the loss of glutaraldehyde. The effect of selecting an alkaline buffer system that is compatible with glutaraldehyde is that the original or starting concentration of glutaraldehyde can be lowered. This in turn decreases the toxicity of the formula.

No acetate salts are added to the glutaraldehyde composition of the present invention, which decreases the acrid fumes and again lowers the overall toxicity of the formula.

It is therefore a primary objective of the present invention to provide an effective chemical disinfectant/sterilant for heat-sensitive medical, dental, and veterinary reusable devices which is stable at alkaline pH values without high concentrations of glutaraldehyde.

It is a further objective of the present invention to provide a chemical disinfectant/sterilant which is free of acetate salts.

It is still a further objective of the present invention to provide a chemical disinfectant/sterilant which does not require an outside source of heat to be tuberculocidal and/or sporicidal.

It is still a further objective of the present invention to provide a chemical disinfectant/sterilant which kills mycobacteria (TB) faster than currently available glutaraldehyde formulations.

It is yet a further objective of the present invention to provide a chemical disinfectant/sterilant which is economical to manufacture and safe to use.

These and other objectives will become apparent from the following description of the invention.

SUMMARY OF THE INVENTION

The present invention relates to an improved disinfectant/sterilant formula of relatively low concentrations of glutaraldehyde (1.0% to 2.0%), plus low concentrations of alcohol (5% to 20%), plus an alkaline buffer system that stabilizes glutaraldehyde so that high concentrations of glutaraldehyde are not necessary. This formula is a sterilant within ten (10) hours at 20° C., and a high-level disinfectant (bactericidal, fungicidal, tuberculocidal, and virucidal) within 20 min. at 20° C. Due to the absence of acetate salts and the lower glutaraldehyde concentration, the fumes of glutaraldehyde are reduced by at least 75% with a concomitant reduction of irritation and toxicity. This formula is effective as a high-level disinfectant within the practical exposure time of twenty (20) min. at ambient temperatures, thus eliminating the need for heating devices.

DETAILED DESCRIPTION OF THE INVENTION

The sterilizing and disinfecting solutions of this invention have a variety of uses. The solutions have excellent sterilization and disinfecting properties and can be used to sterilize sophisticated medical instruments such as endoscopes without causing damage to sensitive parts of such instruments.

The fact that this process can be used with endoscopic instruments is significant since relatively non-invasive endoscopic procedures have revolutionized the way that surgery is performed. Few rigid or flexible endoscopes can be sterilized by the quick and sure method of steam sterilization because the plastic, rubber and precisely- positioned glass lenses of endoscopes make them incompatible with the heat of a steam sterilizer. Instead, they must be sterilized using lower temperatures and typically slower processes. They also must use a sterilizing solution that is non-corrosive.

Endoscopes are but one example of the type of instrument that can be effectively sterilized with the present compositions. Conventional surgical instruments of all types, microsurgery instrument sets, anesthesia equipment, etc. can also be treated. Generally, the composition disclosed herein can be used for sterilization of any products that enter sterile tissue or the vascular system or have tissue contact during any surgeries. Necessarily, if the solution is effective for these critical medical instruments, it also can be used for intermediate level and low level instruments and surfaces. Because the composition has a less acrid odor than conventional glutaraldehyde/acetate salt based sterilants, one can sterilize surfaces that formerly were only disinfected or sanitized, or one can decrease the exposure time for disinfection rather than sterilization. It is therefore versatile in use.

This invention provides a formula for a liquid chemical germicide for high-level disinfection or sterilization for reusable, heat-sensitive medical devices. The formula contains many ingredients and concentrations of ingredients which all work together to provide new and useful features for a glutaraldehyde-based disinfectant/sterilant.

Glutaraldehyde is the first ingredient of the composition and may be present in an amount of between about 1.0% to about 2.0% by volume. This concentration of glutaraldehyde is sporicidal at alkaline pH values. In the present invention, the concentration of glutaraldehyde may be relatively low because other elements of the formula enhance the tuberculocidal activity of glutaraldehyde, and maintain the chemical stability of glutaraldehyde. Antimicrobially active concentrations of glutaraldehyde at 1.0% to 2.0% are much less toxic than the conventional concentrations of 2.5% to 3.5% glutaraldehyde.

Alcohol is the second ingredient of the composition. Appropriate alcohols for use in the present invention are straight-chain water miscible alcohols, including methanol, ethanol, and isopropranol, as well as others. Isopropanol and ethanol are preferred.

The alcohol is present in a concentration of between about 5% to about 20%. The preferred alcohol concentration is 15%. This alcohol concentration greatly enhances the tuberculocidal activity of 1.0% to 2.0% glutaraldehyde. Alcohol alone is not tuberculocidal at 5% to 20%, nor is 1.0% to 2.0% glutaraldehyde tuberculocidal at 20° C. within a practical exposure time of 20 min. However, 5.0% to 20.0% alcohol in combination with 1.0% to 2.0% glutaraldehyde is rapidly tuberculocidal within 20 min. at 20° C. Enhancement of the tuberculocidal activity of glutaraldehyde allows the concentration of glutaraldehyde in the formula to be lowered which in turn makes the composition less irritating and less toxic. Concentrations of alcohol equal to or higher than 30% diminish or inhibit the sporicidal activity of alkaline glutaraldehyde. Therefore, both the presence of alcohol and its low concentration are critical to the performance of the present composition. Chemical stability studies in open trays demonstrated that the concentration of glutaraldehyde and alcohol both remained constant in this formula for 30 days.

The glutaraldehyde concentration remained constant in open trays if the pH was adjusted to 7.0 to 8.0 with a phosphate buffer salt. Buffers other than phosphates caused a 40% drop in glutaraldehyde concentration. Therefore, because the formula of the present invention is buffered with phosphate salts, the glutaraldehyde concentration can be lowered to 1.0% to 2.0% because of the unique composition stability. Examples of phosphate buffers include, but are not limited to, monobasic potassium phosphate, dibasic potassium phosphate, tribasic potassium phosphate, monobasic sodium phosphate, dibasic sodium phosphate, and tribasic sodium phosphate. Generally, the buffer is added in an amount to maintain the composition at a pH of between about 7.0 to 8.9, and preferably from about 7.0 to about 8.0.

The present invention also contemplates that certain ingredients may also be added to the composition to enhance its effectiveness. For instance, anionic, cationic and non-ionic surfactants may be added to the formula to promote a cleaning effect. The amount of surfactant can be within the range of from about 0.05% by volume to about 1.0% by volume, and preferably from about 0.1% by volume to about 0.5% by volume. The amount of surfactant should be enough to enhance sterilization and disinfection, but less than the amount which would provide substantial sudsing.

Suitable synthetic detergents are well known to those of ordinary skill in the art, but generally these surface active agents can be selected from the group consisting of anionic and nonionic surfactants. Non-ionic, ether-linked surfactants such as Laureth®4 or Laureth®23 are preferred.

Alkyl sulfate surfactants are a type of anionic surfactant of importance for use herein. Alkyl sulfates have the general formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), substituted or unsubstituted ammonium cations such as methyl-, dimethyl-, and trimethyl-ammonium and quaternary ammonium cations, e.g., tetramethylammonium and dimethyl piperdinium, and cations derived from alkanolamines such as ethanolamine, diethanolamine, triethanolamine, and mixtures thereof, and the like. Typically, alkyl chains of $C_{12}$–$C_{16}$ are preferred for lower wash temperatures (e.g., below about 50° C.) and $C_{16-18}$ alkyl chains are preferred for higher wash temperatures (e.g., above about 50° C.).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation., Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperydinium and cations derived from alkanolamines, e.g., monoethanolamine, diethanolamine, and triethanolamine, and mixtures thereof. Exemplary surfactants are $C_{12}-C_{18}$ alkyl polyethoxylate (1.0) sulfate, $C_{12}-C_{18}$ alkyl polyethoxylate (2.25) sulfate, $C_{12}-C_{18}$ alkyl polyethoxylate (3.0) sulfate, and $C_{12}-C_{18}$ alkyl polyethoxylate (4.0) sulfate wherein M is conveniently selected from sodium and potassium.

Other types of anionic surfactants can also be included in the compositions hereof. These can include salts (including, for example, sodium, potassium, ammonium, and substituted ammonium salts such as mono-, di- and triethanolamine salts) of soap, $C_9-C_{20}$ linear alkylbenzenesulphonates, $C_8-C_{22}$ primary or secondary alkanesulphonates, $C_8-C_{24}$ olefinsulphonates, sulphonated polycarboxylic acids, alkyl glycerol sulfonates, fatty acyl glycerol sulfonates, fatty oleyl glycerol sulfates, alkyl phenol ethylene oxide ether sulfates, paraffin sulfonates, alkyl phosphates, isothionates such as the acyl isothionates, N-acyl taurates, fatty acid amides of methyl tauride, alkyl succinamates and sulfosuccinates, monoesters of sulfosuccinate (especially saturated and unsaturated $C_{12}-C_{18}$ monoesters) diesters of sulfosuccinate (especially saturated and unsaturated $C_6-C_{14}$ diesters), N-acyl sarcosinates, sulfates of alkylpolysaccharides such as the sulfates of alkylpolyglucoside, branched primary alkyl sulfates, alkyl polyethoxy carboxylates such as those of the formula $RO(CH_2CH_2O)_kCH_2COO-M+$ wherein R is a $C_8-C_{22}$ alkyl, k is an integer from 0 to 10, and M is a soluble salt-forming cation, and fatty acids esterified with isethionic acid and neutralized with sodium hydroxide. Further examples are given in *Surface Active Agents and Detergents* (Vol. I and II by Schwartz, Perry and Berch).

Suitable nonionic detergent surfactants are generally disclosed in U.S. Pat. No. 3,929,678, Laughlin et al, issued Dec. 30, 1975, at column 13, line 14 through column 16, line 6, incorporated herein by reference. Exemplary, non-limiting classes of useful nonionic surfactants are listed below.

The polyethylene, polypropylene, and polybutylene oxide condensates of alkyl phenols can be used. In general, the polyethylene oxide condensates are preferred. These compounds include the condensation products of alkyl phenols having an alkyl group containing from about 6 to about 12 carbon atoms in either a straight chain or branched chain configuration with the alkaline oxide. These compounds are commonly referred to as alkyl phenol alkoxylates, (e.g., alkyl phenol ethoxylates).

The condensation products of aliphatic alcohols with from about 1 to about 25 moles of ethylene oxide can also be used. The alkyl chain of the aliphatic alcohol can either be straight or branches, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol.

Third, the condensation products of ethylene oxide with a hydrophobic base formed by the condensation of propylene oxide with propylene glycol can be used. Examples of compounds of this type include certain of the commercially-available Pluronic™ surfactants, marketed by BASF.

Fourth, the condensation products of ethylene oxide with the product resulting from the reaction of propylene oxide and ethylenediamine may appropriately be used. Examples of this type of nonionic surfactant include certain of the commercially available Tetronic™ compounds, marketed by BASF.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

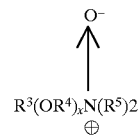

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide groups. The $R^5$ groups can be attached to each other, e.g., through an oxygen or nitrogen atom, to form a ring structure.

These amine oxide surfactants in particular include $C_{10}-C_{18}$ alkyl dimethyl amine oxides and $C_8-C_{12}$ alkoxy ethyl dihydroxy ethyl amine oxides.

Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units, can be used. Any reducing saccharide containing 5 or 6 carbon atoms can be used, e.g., glucose, galactose and galactosyl moieties can be substituted for the glucosyl moieties (optionally, the hydrophobic group is attached at the 2-, 3-, 4-, etc. positions, thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

Fatty acid amide surfactants having the formula:

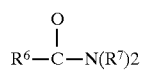

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and —$(C_2H_4O)_xH$ where x varies from about 1 to about 3 can be used.

Nonionic ether linked surfactants are preferred such as Laureth®23 or Laureth®4.

In addition to the above, if desired, corrosion inhibitors at very minor levels can be used, i.e. at levels of 0.01% to about 0.1% on a weight basis. Suitable corrosion inhibitors can include those available and known, for example, complex fatty amine salts such as n,n'dibutylthiourea, etc.

Further, other ingredients such as indicator dyes may be added to the formula. Odorants may also be added to the formula. The only requirement is that the additives be compatible with the other ingredients of the composition. The selection of compatible additives with the compositions of the present invention can be readily ascertained by those of ordinary skill in the art. With the exception of diluents which are used at higher levels. the levels of these minors are generally not more than 0.001% to 0.01% by weight.

The stability of the disinfectant of the present invention offers the advantage over the prior art in that it may be packaged in a single container without activator. The alcohol and glutaraldehyde may also be packaged at a low pH and added to a second package of buffer.

Further, many prior art glutaraldehyde formulas contain salts of acetic acid (vinegar) because they enhance the rate of kill of wet spores in suspension. However, the acetate salts do not help in the dry AOAC Sporicidal Test. Contrary to the belief that it was the glutaraldehyde which was responsible for the offensive odor of these disinfectants, the inventor discovered that disinfectant compositions manufactured without acetate salts had a much less acrid and irritating odor. In addition, the compositions of the present invention are as sporicidal for dry spores without the acetate salts. Moreover, because the compositions are free of acetate salts, the cost of the final product is substantially lower than the cost of compositions containing acetate salts. In fact, it is estimated that the cost of the composition of the present invention, including bottles and labels would not exceed $2.00 per gallon.

The disinfectant/sterilant of the present invention is bactericidal, tuberculocidal, fungicidal, and virucidal within 20 min. at 20° C., and sporicidal within six (6.0) hours at 20° C. Heating devices (water baths, ovens, electrical heating pads) may be used with this formula, but are not necessary for effective antimicrobial activity.

The following examples are provided to illustrate, but not limit, the present invention in any manner.

Historically, the Environmental Protection Agency regulates germicides in the United States, and the test for a sterilizing claim (a sterilant) by a liquid germicide is the Association of Official Analytical Chemists (AOAC) Sporicidal Activity of Disinfectants Test 966.04. This test exposes spores dried onto carrier surfaces to germicide. To make a label claim as a sterilant, a germicide must produce 720 sterile cylinders of 720 total cylinders within a specified exposure time and temperature range. A legal definition of sterilant in the United States is one that can pass this test.

EXAMPLE 1

A typical formula of this invention is as follows:

| | |
|---|---|
| Glutaraldehyde | 1.0% to 2.0% by volume |
| Isopropanol | 5.0% to 20.0% by volume |
| Non-ionic surfactant | 0.05% to 0.5% by volume |
| $Na_2HPO_4$ buffer | 7.2 pH |
| Water | remainder |

EXAMPLE 2

This example demonstrates the enhanced tuberculocidal activity of glutaraldehyde in a composition with 5.0% to 20% alcohol.

| | Surviving Cells of TB[1] Per ml Per Formula | | | | |
|---|---|---|---|---|---|
| Exposure Time In Min. At 20° C. | (A) 2% GA[2] Zero IPA[3] pH 7.7 | (B) 2% GA 20% IPA pH 8.5 | (C) 2% GA 10% IPA pH 8.3 | (D) 2% GA 5% IPA pH 7.8 | (E) Water Control |
| 1 min. | >300 | Zero | 1 | >300 | 5 × 10[5] |
| 5 | 60 | Zero | Zero | Zero | |
| 10 | 5 | Zero | Zero | Zero | |
| 15 | 1 | Zero | Zero | Zero | |
| 20 | 2 | Zero | Zero | Zero | |
| 30 | Zero | Zero | Zero | Zero | |

Notes:
[1]*Mycobacterium bovis* var BCG
[2]GA = Glutaraldehyde
[3]IPA = Isopropanol
Notebook Reference: MicroChem Laboratory NMC-025, pg. 165.

EXAMPLE 3

This example demonstrates that alcohols other than isopropanol also enhance the tuberculocidal activity of glutaraldehyde.

| | Surviving Cells of TB[1] Per ml Per Formula | | | | |
|---|---|---|---|---|---|
| Exposure Time In Min. At 20° C. | (A) 2% GA[2] Zero Alcohol pH 7.6 | (B) 2% GA 15% IPA pH 7.4 | (C) 2% GA 7.5% IPA 7.5% PG pH 7.4 | (D) 2% GA 15% PG[4] pH 7.3 | (E) Water Control |
| 1 min. | 250 × 10[3] | Zero | Zero | Zero | 1.8 × 10[6] |
| 5 | 10 | Zero | Zero | Zero | |
| 10 | 5 | Zero | Zero | Zero | |
| 20 | 2 | Zero | Zero | Zero | |
| 40 | Zero | Zero | Zero | Zero | |

Notes:
[1]*Mycobacterium bovis* var BCG
[2]GA = Glutaraldehyde
[3]IPA = Isopropanol
[4]PG = Propylene Glycol
Notebook Reference: MicroChem Laboratory NMC-023, pg. 203.

EXAMPLE 4

This example demonstrates that concentrations of alcohol greater than 20% interfere with the sporicidal activity of glutaraldehyde, but concentrations of alcohol less than 20% do not interfere with this sporicidal activity.

Percentage of a Group[1] of Spore-Labeled Cylinders[2]
Sterilized as a Function of Exposure Time Per Formula

| Exposure Time In Hrs. At 20° C. | (A) 2% GA[2] No Alcohol pH 7.6 | (B) 2% GA 10% IPA pH 8.4 | (C) 2% GA 20% IPA pH 8.4 | (D) 2% GA 30% IPA pH 8.3 |
|---|---|---|---|---|
| 1 Hrs. | 60% | 27% | 18% | Zero |
| 2 | 57% | 57% | 45% | 13% |
| 4 | 97% | 97% | 92% | 27% |
| 6 | 100% | 100% | 98% | 35% |

Notes:
[1]Thirty (30) spore-labeled cylinders per group
[2]$\geq 10^5$ C. sporogenes spores/unglazed porcelain penicylinder
[3]GA = Glutaraldehyde
[4]IPA = Isopropanol
Notebook Reference: MicroChem Laboratory NMC-025, pg. 95, 101, and 114.

EXAMPLE 5

This example demonstrates two important features of the invention: (1) The chemical stability of the glutaraldehyde depends on the type of buffer used to achieve an alkaline pH value, rather than on the pH value itself; and (2) The alcohol retains at least 75% of its original concentration in an open tray container, and does not rapidly evaporate from the solution.

Glutaraldehyde Conc./Alcohol Conc.

| Days In Open Tray | (A) 2.5% GA[1] Bicarbonate Buffer Zero Alcohol pH 8.6 | (B) 2.5% GA Phosphate Buffer Zero Alcohol pH 7.5 | (C) 2.5% GA E-T-15 Buffer[2] 30% IPA pH 8.8 |
|---|---|---|---|
| 1 | 2.44/Zero | 2.59/Zero | 2.55/29.89 |
| 6 | 1.87/Zero | 2.53/Zero | 2.49/26.6 |
| 13 | 1.62/Zero | 2.53/Zero | 2.48/25.5 |
| 20 | 1.35/Zero | 2.52/Zero | 2.44/24.5 |
| 27 | 1.19/Zero | 2.51/Zero | 2.43/22.4 |

Notes:
[1]GA = Glutaraldehyde
[2]E-T-15 Buffer = Poly (15) oxyethylene amine

The data in the above examples demonstrates an improved sterilant based on several factors including: 1) relatively low concentrations of glutaraldehyde; 2) low concentrations of alcohol; and 3) a glutaraldehyde-stabilizing alkaline buffer system. The low glutaraldehyde concentration offers the benefit of a 50–60% reduction in the amount of glutaraldehyde used in comparison to conventional formulations. This in turn results in a composition which is much less irritating and toxic than conventional 2.5–3.5% glutaraldehyde formulations.

Second, the elimination of acetate salts from the sterilizing composition eliminates the acrid odor from the acetates and also makes the formulation less irritating, malodorous, and toxic.

Third, the 10–20% alcohol concentration has rapid tuberculocidal activity. The soak/exposure time for high-level disinfection is about 20 minutes at 20° C., and may be as short as 10 minutes at 20° C. Further, it is not necessary to heat the formulation to 25° C. in order to get this tuberculocidal effect, although it is permitted.

Fourth, the phosphate buffer system stabilizes the glutaraldehyde such that the glutaraldehyde concentration can be lowered below 2.5%. Because of this, the use/re-use life of the composition is longer and the margins of safety are greater.

Further, the pH of the composition of from about 7.0 to about 8.9 makes it compatible with virtually all immersible materials.

For the above reasons, it is submitted that the above invention accomplishes at least all of its stated objectives.

What is claimed is:

1. An aqueous, room temperature disinfecting and/or sterilization solution having a pH of from about 7.0 to about 8.9 consisting of:
   from about 1.0% to about 2.0% glutaraldehyde by volume;
   from about 5.0% to about 20.0% alcohol by volume, wherein the alcohol is selected from the group consisting of methanol, ethanol, isopropanol, and polyethylene glycol;
   a phosphate buffer;
   a surfactant;
   the remainder of the solution being water;
   and further providing that the solution contains insufficient acetate salts to make the solution irritating, malodorous, or toxic.

2. An aqueous disinfecting and/or sterilization solution according to claim 1 wherein the alcohol concentration is 10% by volume or less.

3. An aqueous disinfecting and/or sterilizing solution according to claim 1 wherein the phosphate buffer is dibasic sodium phosphate.

4. An aqueous disinfecting and/or sterilization solution according to claim 1 further including a surfactant selected from the group consisting of nonionic, cationic and anionic surfactants.

5. An aqueous disinfecting and/or sterilization solution according to claim 1 wherein the surfactant is in a concentration of from about 0.05 to about 0.5% by volume.

6. An aqueous disinfecting and/or sterilization solution according to claim 1 wherein the surfactant is a nonionic surfactant.

7. An aqueous disinfecting and/or sterilization solution according to claim 1 which is substantially free of acetate salts.

8. An aqueous disinfecting and/or sterilization solution according to claim 1 wherein the concentration of glutaraldehyde is from about 1.25% to about 1.50% by volume.

9. An aqueous disinfecting and/or sterilization solution according to claim 1 wherein the pH of the solution is about 7.2.

* * * * *